United States Patent [19]

Uohama et al.

[11] Patent Number: 4,948,916
[45] Date of Patent: Aug. 14, 1990

[54] PROCESS FOR PRODUCING AMINOOXYACETIC ACID SALTS

[75] Inventors: Misao Uohama; Youichirou Tani, both of Chiba, Japan

[73] Assignee: Dainippon Ink and Chemicals, Inc., Tokyo, Japan

[21] Appl. No.: 241,422

[22] Filed: Sep. 7, 1988

[30] Foreign Application Priority Data

Sep. 8, 1987 [JP] Japan ................................ 62-222937

[51] Int. Cl.$^5$ ............................................. C07C 83/10
[52] U.S. Cl. ................................................... 560/515
[58] Field of Search ................ 560/315; 260/500.5 H; 562/579

[56] References Cited

U.S. PATENT DOCUMENTS

| 3,364,110 | 1/1968 | Lehr et al. | 560/315 |
| 3,457,063 | 7/1969 | Neighbours | 71/115 |
| 3,504,008 | 3/1970 | Neighbors | 560/315 |

FOREIGN PATENT DOCUMENTS 2150778 4/1973 France .

OTHER PUBLICATIONS

Journal of the Chemical Society, vol. II, 1960, pp. 225–229.
Helvitica Chimica Acta, vol. 52, No. 3, 1969, pp. 569–576, Schweizerische Chemische Gesellschaft, Basel, CH.
Chemical Abstracts, vol. 67, 1967, p. 10210, Abstract No. 108398h, V. I. Ivanov et al.
Chemical Abstracts, vol. 89, 1978, p. 845, Abstract No. 108740t, V. I. Ivanov et al.
Chemical Abstracts, vol. 95, 1981, p. 772, Abstract No. 151159w.

*Primary Examiner*—Mary C. Lee
*Assistant Examiner*—Robert C. Whittenbaugh
*Attorney, Agent, or Firm*—Armstrong, Nikaido, Marmelstein, Kubovcik & Murray

[57] ABSTRACT

A process for producing an aminooxyacetic acid salt comprises reacting benzhydroxamic acid of formula:

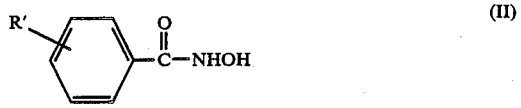

(II)

(where $R^1$ is a hydrogen atom, an alkyl group, an alkoxy group or a halogen atom) with a halogenoacetic acid of formula:

$$XCH_2CO_2H \qquad (III)$$

(where X is an iodine, bromine or chlorine atom) in the presence of a metal hydroxide or a metal carbonate to form benzamidooxyacetic acid of formula (IV):

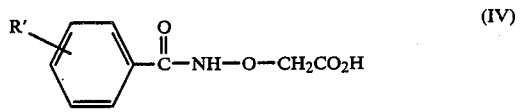

(IV)

and thereafter hydrolyzing the benzamidooxyacetic acid in the presence of a mineral acid to obtain an aminooxyacetic acid salt of formula:

$$2H_2NOCH_2CO_2H \cdot A \qquad (V)$$

8 Claims, No Drawings

PROCESS FOR PRODUCING AMINOOXYACETIC ACID SALTS

BACKGROUND OF THE INVENTION

The present invention relates to a process for producing aminooxyacetic acid salts which are useful as intermediates for the production of pharmaceuticals, agrichemicals and other chemicals.

While several methods are known in the art of producing aminooxyacetic acid, the following are representative: (1) aldoxime or ketoxime is reacted with a halogenoacetic acid and the resulting oxime-O-acetic acid is either hydrolyzed with an acid or reacted with hydrazine to obtain aminooxyacetic acid [Org. Syn. Coll., vol. 3,172 (1955); and Atti. soc. peloritana sci. fis. mat. e net, 4, 147 (1957)]; (2) an acid anhydride is reacted with hydroxylamine to obtain N-hydroxyimide, which is reacted with a halogenoacetic acid, and hydrazine is allowed to act on the reaction product to obtain aminooxyacetic acid [Bull. Soc. Chim. Fr., 833 (1976)]; (3) tert-butyl N-hydroxycarbamate is reacted with a halogenoacetic acid to obtain oxime-0-acetic acid, which then is decomposed with an acid to obtain aminooxyacetic acid (British Patent No. 1,394,170); (4) benzhydroxamic acid is reacted with an ester of a halogenoacetic acid to form a benzamidooxyacetic acid ester, which is hydrolyzed with an acid to obtain aminooxyacetic acid [J. Biochem. Japan, 23, 181 (1936)]; and (5) benzhydroxamic acid is reacted with α-halogenoacetic acid in absolute ethanol in the presence of metallic sodium and the reaction product is hydrolyzed in a solution of hydrochloric acid and glacial acetic acid to obtain aminooxyacetic acid (Unexamined published Japanese Patent Application No. 56-43245).

These conventional methods are defective in one way or another in that they attain only low yields or involve complicated reaction procedures such that the reactions are conducted under anhydrous conditions. Furthermore, these methods are not suitable for application to industrial operations since they employ expensive bromoacetic acid or reagents, such as phenylhydrazine or metallic sodium, which requires great care to avoid potential danger.

The present inventors, therefore, conducted intensive studies in order to eliminate these defects of the prior art and to establish an industrially feasible process for producing aminooxyacetic acid. As a result, the present inventors found that when a halogenoacetic acid, instead of an easter thereof, was reacted with benzhydroxamic acid in the presence of a metal hydroxide or a metal carbonate, benzoamidooxyacetic acid could be obtained in high yield while requiring simple reaction procedures. The present invention has been accomplished on the basis of this finding.

SUMMARY OF THE INVENTION

According to the present invention there is provided a process for producing an aminooxyacetic acid salt which comprises reacting benzhydroxamic acid of formula (II):

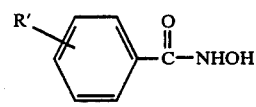
(II)

wherein $R^1$ is a hydrogen atom, an alkyl group, an alkoxy group or a halogen atom, with a halogenoacetic acid of formula (III):

$$XCH_2CO_2H \qquad (III)$$

wherein X is an iodine, bromine or chlorine atom, in the presence of a metal hydroxide or a metal carbonate to form benzamidooxyacetic acid of formula (IV):

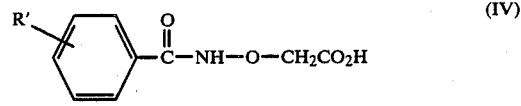
(IV)

wherein $R^1$ is the same as $R^1$ in the general formula (II), and thereafter hydrolyzing the benzamidooxyacetic acid in the presence of a mineral acid to obtain an aminooxyacetic acid salt of formula (V):

$$2H_2NOCH_2CO_2H \cdot A \qquad (V)$$

wherein A is HI, HBr, HCl or ½ $H_2SO_4$.

DETAILED DESCRIPTION OF THE INVENTION

The benzhydroxamic acid of the general formula (II) which is used as a starting material in the process of the present invention may be prepared by reacting an aromatic carboxylic acid derivative of the following formula (I):

(I)

wherein $R^1$ is the same as in the formula (II), and $R^2$ is an alkoxy group or a halogen atom, with hydroxylamine. From an economic viewpoint and because of the possibility of obtaining a benzamidooxyacetic acid that readily dissolves and is hydrolyzed in the presence of a mineral acid, $R^1$ in the formula (I) is preferably a hydrogen atom. As for $R^2$ in the formula (I), a lower aliphatic alkoxy group such as methoxy, ethoxy or propoxy is preferred in view of the ease of treatment following the reaction with hydroxylamine.

The reaction between the aromatic carboxylic acid derivative (I) and hydroxylamine is performed either in a solvent that is capable of dissolving the reactants or in a mixture of this solvent and water. Preferred solvents are lower aliphatic alcohols such as methyl alcohol, ethyl alcohol, n-propyl alcohol, isopropyl alcohol and n-butyl alcohol. The reaction can be carried out at a temperature of 0–100° C. until it is substantially completed. The molar ratio of the aromatic carboxylic acid derivative to hydroxylamine is such that hydroxylamine is in slight excess of the aromatic carboxylic acid derivative, and the preferred ratio is 1.0 to 1.0–1.5.

Hydroxylamine used as a starting material may be in the form of either a salt of a mineral acid such as hydrochloric acid or sulfuric acid or an aqueous solution in which it is present in a free state. Although there is no particular limitation on the form in which hydroxylamine is used, it must be rendered free by addition of a base prior to reaction if the latter is to be performed using a mineral acid salt of hydroxylamine.

After the reaction, the resulting benzhydroxamic acid represented by the formula (II) may be directly used (without being isolated) as a starting material for the reaction with a halogenoacetic acid in the next step. If desired, the benzhydroxamic acid may be isolated before it is used as a starting material for the reaction in the subsequent step. In this latter case, the solvent is recovered after completion of the reaction and the precipitating benzhydroxamic acid is either recovered by filtration or extracted with a suitable solvent such as ethyl acetate, diethyl ether, dichloromethane or chloroform. However, in the present invention, the subsequent step for reaction with a halogenoacetic acid is performed using as a base a metal hydroxide or a metal carbonate which do not require dry reaction conditions. Therefore, the benzhydroxamic acid formed as a result of reaction between the aromatic carboxylic acid derivative (I) and hydroxylamine need not be isolated and may be directly subjected to the subsequent step in the form of a water-containing solution. This method is very advantageous not only in economic terms but also from the viewpoint of operational efficiency.

Thus prepared benzhydroxamic acid represented by the formula (II) is subsequently reacted with a halogenoacetic acid of the formula (III) so as to be converted to a benzamidooxyacetic acid of the formula (IV). In the formula (III), X is selected from iodine, bromie and chlorine atoms and a chlorine atom is preferred from the viewpoints of the ease of reaction and economy. The reaction is performed in a solvent in the presence of a metal hydroxide or a metal carbonate at a temperature in the range of from 0° to 100° C., preferably from 40° to 80° C. Preferred metal hydroxides and alkali metal or alkaline earth metal hydroxides such as NaOH, KOH, LiOH and Ca(OH)$_2$. Preferred metal carbonates are alkali metal carbonates such as Na$_2$CO$_3$, K$_2$CO$_3$ and Li$_2$CO$_3$. These metal hydroxides or metal carbonates are used in amounts that normally range from 1.5 to 6.0 moles, preferably from 2.0 to 3.0 moles, per mole of benzhydroxamic acid.

The molar ratio of benzhydroxamic acid to halogenoacetic acid is normally in the range of from 1:1 to 1:2, preferably from 1:1 to 1:1.3. Suitable reaction solvents are polar solvents including lower aliphatic alcohols (e.g. methyl alcohol and ethyl alcohol) and dimethylformamide, as well as mixtures of these solvents with water. A particularly preferred solvent is methyl alcohol or a mixture thereof with water.

After the reaction, the solvent is recovered and the residue is acidified with a mineral acid, and thereafter, the resulting the benzamidooxyacetic acid which is represented by the formula (IV) is recovered by filtration or extracted with an organic solvent such as ethyl acetate, diethyl ether, dichloromethane or chloroform.

The prepared benzamidooxacetic acid is converted to a corresponding aminooxacetic acid by standard procedures of hydrolysis in the presence of a mineral acid. The reaction for effecting this conversion is performed in an aqueous solution at a temperature within the range of 40°–100° C. The mineral acid is used at a concentration which ranges from 5 to 50 wt %, preferably from 10 to 20 wt %. If the concentration of mineral acid exceeds 50 wt %, undesired side reactions will occur. The solvent is used in an amount that normally ranges from 1 to 50 times, preferably from 5 to 10 times, the amount of benzoamidooxyacetic acid.

After completion of the reaction, the by-product substituted or unsubstituted benzoic acid is filtered off. When the solvent is recovered from the filtrate, the desired aminooxyacetic acid salt is obtained as a residue. Benzoic acids can be recovered in substantially stoichiometric amounts and may be subjected to cyclic use as a starting material for the production of benzhydroxamic acid by being esterified or converted to acid halides.

If desired, the aminooxacetic acid salt obtained may be further purified. While purification may be performed by column chromatography, a recrystallization method is preferred since it is adapted for industrial operations. A solvent for recrystallization is either water or a mixture thereof with an organic solvent. Preferred examples of organic solvents are polar solvents including lower aliphatic alcohols such as methyl alcohol, ethyl alcohol and isopropyl alcohol, as well as tetrahydrofuran, dimethylformamide and dimethoxyethane. Isopropyl alcohol is particularly preferred since it provides high yield. The weight ratio of aminooxacetic acid salt to water to organic solvent is normally in the range of 1:1–10:1–20, preferably 1:1–3:5–10. Recrystallization of the aminooxyacetic acid salt may comprise dissolving it in water either at room temperature or under heating and cooling the solution to obtain crystal. When an organic solvent is used, the solvent may be added to an aqueous solution of the aminooxyacetic acid salt, followed by cooling the solution to obtain the purified product of the salt.

As described above, the process of the present invention enables an aminooxyacetic acid salt to be obtained in high yield by simple reaction procedures using industrially available inexpensive starting materials. Since benzoic acids used as a starting material can be recovered in sufficiently high yield to be cyclically used after reaction, the process of the present invention offers additional advantages including economy and adaptability for industrial operations.

The following examples and comparative examples are provided for the purpose of further illustrating the present invention but are in no way to be taken as limiting. Unless otherwise noted, all percents in the following examples and comparative examples are not on a weight basis.

EXAMPLE 1

(1) Preparation of benzhydroxamic acid 8.2 Grams (0.05 moles) of hydroxylamine sulfate was dissolved in 20 ml of water. Under cooling with ice, 10 g (0.1 mole) of an aqueous solution of 40% sodium hydroxide was slowly added dropwise to form free hydroxylamine. After completion of the addition, a mixture of 13.6 g (0.1 mole) of methyl benzoate and 80 ml of methanol was added at a time and the so prepared reaction solution was heated under reflux for 6 hours. After distilling off methyl alcohol under vacuum, concentrated hydrochloric acid was added to the remaining aqueous solution so as to adjust its pH to 7.

50 ml ethyl acetate was added to the solution and the separating organic layer was washed twice with 50 ml of a saturated solution of sodium chloride. By distilling off ethyl acetate under vacuum benzhydroxamic acid (m.p. 125 127° C.) was obtained in an amount of 12.2 g (yield, 89 mol %).

(2) Preparation of benzamidooxyacetic acid 13.7 Grams (0.1 mole) of benzhydroxamic acid and 8.8 g (0.1 mole) of chloroacetic acid were dissolved in 60 ml of methyl alcohol. To the resulting solution, 20 g (0.2 moles) of 40% aqueous solution of sodium hydroxide was slowly added dropwise. After completion of the addition, the reaction solution was heated under reflux for 8 hours and subsequently cooled. After distilling of methyl alcohol under vacuum, concentrated hydrochloric acid was added to the remaining aqueous solution so as to adjust pH to 1. Ethyl acetate (50 ml) was added to the solution. The separated organic layer was washed twice with 50 ml of a saturated sodium chloride solution. By distilling off ethyl acetate, benzamidooxyacetic acid (m.p. 144°145° C.) was obtained in an amount of 18.2 g (yield, 93 mol %).

(3) Preparation of aminooxyacetic acid hydrochloride 19.5 Grams (0.1 mole) of benzamidooxyacetic acid was suspended in 100 ml of 4 N HCl and heated at 80°–85° C. for 2 hours with stirring. The benzamidooxyacetic acid dissolved completely at about 40° C. The reaction solution was cooled down near to room temperature. The precipitating benzoic acid wa filtered off. The benzoic acid was recovered in an amount of 12.2 g (yield, 99 mol % with respect to benzamidooxyacetic acid). By distilling off water from the filtrate under vacuum, a crude product of aminooxyacetic acid hydrochloride was obtained in an amount of 10.2 g (yield, 94%).

(4) Purification of aminooxyacetic acid hydrochloride 10.9 Grams (0.1 mole) of the crude aminooxyacetic acid hydrochloride was added to 11 ml of water and dissolved therein by heating at 40° C. After adding 100 ml of isopropyl alcohol, the solution was stirred for 1 hour under cooling at 0°–10° C. The precipitating crystal was recovered by filtration to obtain a purified product of aminooxyacetic acid hydrochloride (m.p. 144°–145° C.) in an amount of 9.8 g (yield, 90 mol %).

EXAMPLE 2

Using benzoyl chloride in place of methyl benzoate, benzhydroxamic acid was prepared by the following procedures. 3.3 Grams (0.1 mol) of free hydroxylamine was formed as in Example 1(1). To the solution, 53 g (0.05 moles) of a 10% aqueous solution of sodium hydrogencarbonate was added, and then 14 g (0.1 mole) of benzoyl chloride was slowly added dropwise with the temperature held no higher than 10° C. After completion of the addition of benzoyl chloride, the mixture was stirred at room temperature for 1 hour. The resulting precipitate was recovered by filtration, washed with 30 ml of water and dried to obtain a mixture of benzhydroxamic acid and benzoic acid in amounts of 11.1 g (yield, 81 mol %) and 1.8 g (yield, 13 mol %), respectively.

Subsequently, the procedures of Example 1(2), (3) and (4) were repeated to obtain a purified product of aminooxyacetic acid hydrochloride except that 13.7 g of benzhydroxamic acid used in Example 1(2) was used in place of 15.9 g of the above-described mixture containing 13.7 g of benzhydroxamic acid.

EXAMPLE 3

Benzhydroxamic acid was prepared as in Example 1(1). Thereafter, benzamidooxyacetic acid was obtained in amount of 18.6 g (yield, 95 mol %) by repeating the procedures of Example 1(2) except that 13.8 g (0.1 mole) of bromoacetic acid was used in place of 8.8 g (0.1 mole) of chloroacetic acid. Subsequently, the procedures of Example 1(3) and (4) were repeated to obtain a purified product of aminooxyacetic acid hydrochloride.

EXAMPLE 4

By performing synthesis of benzhydroxamic acid as in Example 1(1), a reaction solution containing 12.2 g (0.089 moles) of benzhydroxamic acid was obtained. Without isolating the benzhydroxamic acid, 7.8 g (0.089 moles) of chloroacetic acid was added to said reaction solution and 18 g (0.18 moles) of 40% aqueous solution of sodium hydroxide was slowly added dropwise to the mixture. After completion of the addition of aqueous NaOH solution, the reaction solution was heated under reflux for 8 hours. After completion of the reaction, post-treatment was conducted as in Example 1(2) to obtain 16.0 g of benzamidooxyacetic acid (yield, 82 mol % based on methyl benzoate and 92 mol % based on benzhydroxamic acid).

Subsequently, the procedures of Example 1(3) and (4) were repeated to obtain a purified product of aminooxyacetic acid hydrochloride.

EXAMPLES 5-7

Substituted benzamidooxyacetic acid was obtained as in Example 4 except that 16.1 g (0.1 mole) of methyl p-chlorobenzoate (in Example 5) or 15 g (0.1 mole) of methyl p-methylbenzoate (in Example 6) or 16.6 g (0.1 mole) of methyl p-methoxybenzoate (in Example 7) was used respectively in place of 13.6 g (0.1 mole) of the starting methyl benzoate. Subsequently, the procedures of Example 1(3) and (4) were repeated to obtain a purified product of aminooxyacetic acid hydrochloride.

The yield of substituted benzamidooxyacetic acid based on the starting material and that of the crude aminooxyacetic acid hydrochloride based on the substituted benzamidooxyacetic acid are shown in Table 1 below for each of Examples 5 to 7.

TABLE 1

| | Yield (Mol %) | |
|---|---|---|
| Example | Substituted benzamidooxyacetic acid | Crude aminooxyacetic acid hydrochloride |
| 5 | 79 | 92 |
| 6 | 83 | 95 |
| 7 | 84 | 90 |

Benzamidooxyacetic acid was obtained as in Examples 1(1) and (2). Thereafter, an oil of crude aminooxyacetic acid sulfate was obtained in an amount of 14.9 g (yield, 79 mol) by repeating the procedures of Example 1(3) except that 100 ml of 4 N HCL was used in place of 100 ml of 2 N sulfuric acid.

COMPARATIVE EXAMPLE 1

(1) Preparation of acetone oxime 108.3 Grams (1.56 moles) of hydroxylamine hydrochloride was dissolved in 600 ml of water, and 85 g (0.80 moles) of sodium carbonate was added to the solution while maintaining a temperature at not higher than 30° C. To the resulting mixture, 88 g (1.52 moles) of acetone was added at a time and stirred for 12 hours at 22°–24° C. The reaction solution was saturated with sodium chloride and extraction was performed three times with 200 ml of toluene. The extract wa dried with magnesium sulfate and the solvent was distilled off under vacuum. By distilling the residue at atmospheric pressure, acetone oxime (b.p. 136° C.; m.p. 60° C.) was obtained in an amount of 74.4 g (yield, 67 mol %).

(2) Preparation of isopropylidene aminooxyacetic acid 47.3 Grams (0.5 moles) of chloroacetic acid was dissolved in 55 g (0.55 moles) of an aqueous solution of 40% sodium hydroxide. To the solution, 36.5 g (0.5 moles) of acetone oxime was added, and then 55 g (0.55 moles) of an aqueous solution of 40% sodium hydroxide was added dropwise to the mixture while maintaining a temperature at not higher than 30° C. Reaction was subsequently performed with the solution being allowed to flow at a rate of 4 ml/min into a glass tube (10 mm in diameter and 100 mm in length) that was heated at 90°-100° C. The unreacted acetone oxime was removed from the reaction solution by two extractions with 100 ml of ether. The pH of the remaining aqueous solution was adjusted to 1 with concentrated HCl. The solution was subsequently saturated with sodium chloride. The resulting aqueous solution was subjected to two extractions with 100 ml of ether and the extract was dried with magnesium sulfate. Ether was distilled off under vacuum and the residue was distilled under vacuum to obtain isopropylidene aminooxyacetic acid (m.p. 76° C.) in an amount of 16.3 g (yield, 25 mol %).

(3) Preparation of aminooxyacetic acid hydrochloride

13 Grams (0.1 mole) of isopropylidene aminooxyacetic acid was added to 100 ml of 6N HCl and the mixture was refluxed for 3 hours. Then, water was distilled off under vacuum and the residue was concentrated to 10 ml. To the concentrated residue, 100 ml of a 1:1 (by volume) mixture of ethyl alcohol and ether was added and left to stand at 0°-5° C. for 12 hours. The precipitating crystal was recovered by filtration and dried under vacuum to obtain aminooxyacetic acid hydrochloride in an amount of 2.6 g (yield, 23 mol %).

COMPARATIVE EXAMPLE 2

(1) Preparation of benzamidooxyacetic acid 9.2 Grams (0.4 moles) of metallic sodium was dissolved in 300 ml of absolute ethanol. To the resulting solution, a solution of 27 g (0.2 moles) of benzhydroxamic acid in 600 ml of absolute ethanol was added dropwise 20°-25° C. with stirring for 3 hours. Subsequently, a solution of 9.5 g (0.1 mole) of chloroacetic acid in 100 ml of absolute ethanol was added dropwise and the resulting mixture wa stirred at 50° C. for 8 hours. After cooling the mixture, water was added and the mixture was neutralized with concentrated HCl. Ethanol was distilled off under vacuum and the pH of the residue was adjusted to 1 by addition of concentrated HCl. The precipitating crystal was recovered by filtration and dried to obtain benzamidooxyacetic acid in an amount of 8.2 g (yield, 42 mol %).

(2) Preparation of aminooxyacetic acid hydrochloride 9.6 Grams (0.05 moles) of benzamidooxyacetic acid was added to 100 ml of a 1:1 (by volume) mixture of conc. HCl and glacial acetic acid and the resulting solution was stirred at 21°-24° C. for 20 hours. The by-product benzoic acid was removed by extraction with ethyl acetate and the aqueous layer was concentrated under vacuum. To the residue, 50 ml of isopropyl alcohol was added and the mixture was stirred for 1 hour with cooling at 0°-10° C. The precipitating crystal was recovered by filtration and dried to obtain aminooxyacetic acid hydrochloride in amount of 4.7 g (yield, 86 mol %).

While the invention has been described in detail and with reference to specific embodiments thereof, it will be apparent to one skilled in the art that various changes and modifications can be made therein without departing from the spirit and scope thereof.

What is claimed is:

1. A process for producing an benzamidooxyacetic acid salt which comprises reacting benzhydroxamic acid of formula (II):

$$R'\text{-C}_6H_4\text{-C(=O)-NHOH} \quad (II)$$

wherein $R^1$ is a hydrogen atom, an alkyl group, an alkoxy group or a halogen atom, with chloroacetic acid in the presence of a metal hydroxide or a metal carbonate to form benzamidooxyacetic acid of formula (IV):

$$R'\text{-C}_6H_4\text{-C(=O)-NH-O-CH}_2\text{CO}_2\text{H} \quad (IV)$$

wherein $R^1$ is the same as in formula (II).

2. A process according to claim 1, wherein said metal hydroxide or metal carbonate is NaOH, KOH, LiOH, Ca(OH)$_2$, Na$_2$CO$_3$, K$_2$CO$_3$, or Li$_2$CO$_3$.

3. A process according to claim 1, wherein said metal hydroxide or metal carbonate is used in an amount of 1.5-6.0 moles per mole of benzhydroxamic acid.

4. A process according to claim 1, wherein the reaction between benzhydroxamic acid and chloroacetic acid is performed in a polar solvent or a mixture thereof with water.

5. A process according to claim 1, wherein the benzhydroxamic acid is prepared by reacting hydroxylamine with an aromatic carboxylic acid derivative of formula (I):

$$R'\text{-C}_6H_4\text{-C(=O)-R}^2 \quad (I)$$

wherein $R^1$ is a hydrogen atom, and $R^2$ is a lower alkoxy group or a halogen atom.

6. A process according to claim 5, wherein the reaction between the aromatic carboxylic acid and hydroxylamine is performed in a lower aliphatic alcohol or a mixture thereof with water.

7. A process according to claim 1, which further comprises hydrolyzing the benzamidooxyacetic acid of formula (IV) with a mineral acid to obtain an aminooxyacetic acid salt of formula:

2H$_2$NOCH$_2$CO$_2$H·A wherein A is HI, HBr, HCl or ½H$_2$SO$_4$.

8. A process according to claim 7, wherein the mineral acid is hydrochloric acid.

* * * * *